United States Patent
Johnson et al.

(10) Patent No.: US 9,649,422 B2
(45) Date of Patent: May 16, 2017

(54) MONITORING AND DETECTING EMPTY FLUID CONTAINERS IN A BLOOD PROCESSING SYSTEM

(75) Inventors: Timothy A. Johnson, Issaquah, WA (US); David L. Bonnett, Reading, MA (US); Robert J. Cantu, West Chester, OH (US); Russell D. Stinaff, Chicago, IL (US); Carole Lynn Stinaff, legal representative, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 564 days.

(21) Appl. No.: 13/557,908

(22) Filed: Jul. 25, 2012

(65) Prior Publication Data

US 2012/0285545 A1    Nov. 15, 2012

Related U.S. Application Data

(62) Division of application No. 12/394,384, filed on Feb. 27, 2009, now abandoned.

(60) Provisional application No. 61/031,970, filed on Feb. 27, 2008.

(51) Int. Cl.
| | |
|---|---|
| *B67D 1/00* | (2006.01) |
| *B67D 7/14* | (2010.01) |
| *A61M 1/36* | (2006.01) |

(52) U.S. Cl.
CPC ........ *A61M 1/36* (2013.01); *A61M 2205/3386* (2013.01); *A61M 2205/3393* (2013.01); *Y10T 137/0318* (2015.04)

(58) Field of Classification Search
USPC .......................................... 222/58, 59, 66, 77
See application file for complete search history.

(56) References Cited

U.S. PATENT DOCUMENTS

| | | | |
|---|---|---|---|
| 4,384,578 A | * | 5/1983 | Winkler ........................ 604/114 |
| 4,646,784 A | | 3/1987 | de Leeuwe |
| 4,778,450 A | | 10/1988 | Kamen |
| 6,581,801 B2 | | 6/2003 | Gauthier |
| 2010/0280430 A1 | * | 11/2010 | Caleffi et al. ................ 604/5.01 |
| 2013/0233394 A1 | * | 9/2013 | Nguyen .................... A61J 1/20 137/2 |

* cited by examiner

*Primary Examiner* — Patrick M Buechner
*Assistant Examiner* — Jeremy W Carroll
(74) *Attorney, Agent, or Firm* — Cook Alex Ltd.

(57) ABSTRACT

Systems and methods for determining when a fluid supply container of a blood processing apparatus becomes empty. The system uses a scale to monitor and detect when a fluid supply container is empty based on the rate of change of the container weight, and a controller receives a signal from the scale and controls the operation of a pump to stop pumping when the fluid supply container is empty.

12 Claims, 3 Drawing Sheets

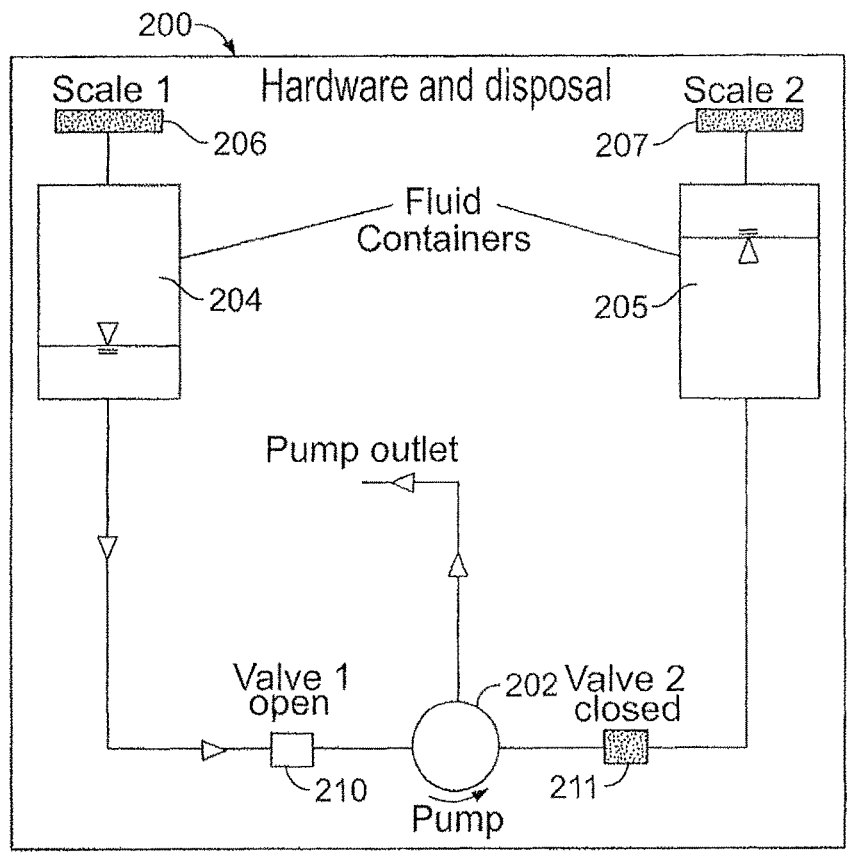
FIG. 2
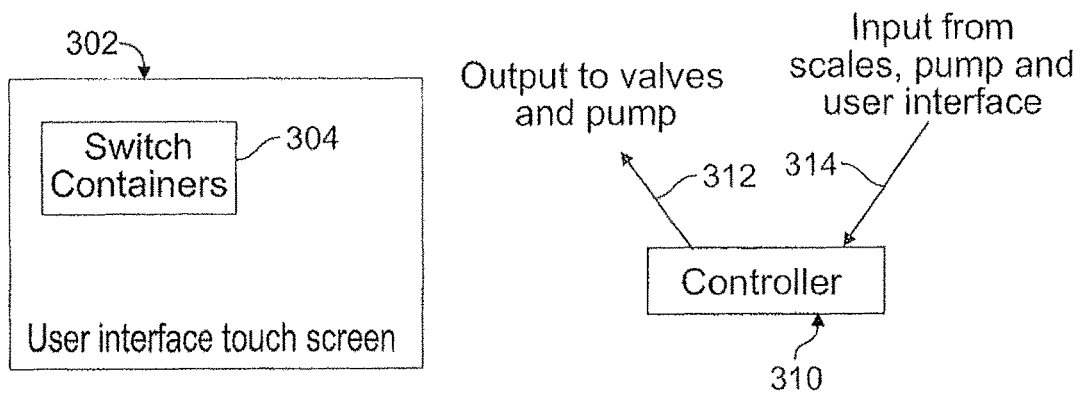
FIG. 3A
FIG. 3B

MONITORING AND DETECTING EMPTY FLUID CONTAINERS IN A BLOOD PROCESSING SYSTEM

CROSS-REFERENCE TO RELATED APPLICATION

This application is a division of U.S. patent application Ser. No. 12/394,384, filed Feb. 27, 2009, which claims priority from U.S. Provisional Patent Application No. 61/031,970, filed Feb. 27, 2008, both of which are incorporated by reference herein in their entirety.

FIELD OF THE INVENTION

The present disclosure relates generally to methods and apparatus for monitoring and detecting empty fluid containers, and more particularly, to methods and apparatus for monitoring and detecting empty fluid containers used with a blood processing or apheresis instrument.

BACKGROUND OF THE INVENTION

Often, a blood processing or apheresis instrument is used to separate blood components from whole blood. Such apheresis instruments are commercially available from various sources, including the Amicus® instrument which is available from Fenwal Inc., of Lake Zurich, Ill. Such instruments, also known as "separators", typically separate a selected blood component from whole blood by passing the blood of a donor through the instrument to separate one or more blood components from the whole blood. The remainder of the whole blood is then returned to the circulatory system of the donor. It is, therefore, an extracorporeal blood component collection process.

Instruments such as the Amicus instrument may utilize a disposable apheresis kit for collection of a desired blood component. The instrument may have pumps, clamps, and valves that move and direct donor blood through the kit. Such kits are often referred to as "disposables". Connected to such a kit may be one or more fluid supply containers of replacement fluids for infusion into the donor. Indeed, a therapeutic plasma exchange (TPE) procedure may require multiple containers of fluid to replace potentially up to three or more liters of the patient's waste plasma.

During an apheresis procedure, one of the most significant concerns is prevention of an air embolism. To reduce the risk of air embolism, it is vital to ensure that air does not enter the apheresis disposable kit during a blood component collection procedure. For example, air can be drawn into the disposable kit during a collection procedure when the fluid source, or fluid supply container attached to the kit becomes exhausted of fluid.

During therapeutic plasmapheresis, a patient's plasma is continuously removed while normal plasma or albumin (replacement fluid) is continuously infused. In current practice, two replacement fluid supply containers are usually connected to the disposable kit. Replacement fluid is drawn from one container while the other container is clamped. The operator must closely monitor the fluid level in the "active" container. When this container empties, the operator must close its clamp while opening the clamp on the other container. If the operator is occupied with the patient, or otherwise distracted, and does not perform this operation, a large volume of air may be drawn into the disposable kit, requiring air to be purged.

Apheresis instruments are typically equipped with air detection systems that continually monitor the fluid that is being returned to the donor/patient. If, during a procedure, air reaches the air detection system, blood processing is interrupted until the air is purged from the system. Often multiple air purges are required to clear this air. Since blood is not being processed during these purges, the overall efficiency of the blood collection procedure is decreased.

A general object of the present disclosure is to therefore provide apparatus and methods for automatically determining when a fluid container becomes empty and to terminate further use of the empty container.

Another object of the present disclosure is to provide apparatus and methods for determining when a fluid container becomes empty independent of the size, volume or composition of matter of the container.

A further object of the present disclosure is to provide a system for determining when the rate of change of the weight of the container and its fluid is less than expected.

Yet another object of the present disclosure is to automatically begin pumping from a second container when it is determined that a first container is empty.

A still further object of the present disclosure is to provide apparatus for determining when a fluid container becomes empty independent of flow rate from the container.

SUMMARY OF THE INVENTION

The present disclosure is directed to apparatus and methods of using weight scales, a pump and a controller to detect, as quickly as possible, an empty fluid supply container. The apparatus identifies the time at which the rate of change of the weight of the container is less than expected based on a known pump rate. The pump that is drawing fluid from the now empty fluid container is then commanded to stop pumping from the container before air enters a blood collection kit. If using two fluid supply containers, the apparatus can be made to automatically start pumping from the second container when it determines that the first container is empty. By analyzing the rate of change of the weight of the container, the apparatus can work independently of the container used, including for instance, independently of container size, volume or composition (plastic or glass, flexible or rigid), as well as independently of the flow rate. This is especially important in therapeutic plasma exchange (TPE) procedures since TPE operators may use many different replacement fluid supply container configurations during a single procedure, and may operate at different flow rates.

The improved monitoring of empty fluid supply containers with the present methods and apparatus keeps air from being pumped into the blood collection kit from an empty container and substantially decreases the need to perform air purges. Thus, procedural efficiency is increased. It also may automate switching between two replacement fluid supply containers during therapeutic plasmapheresis, which allows the operator to concentrate on the patient and not the amount of fluid remaining in a container currently being used.

BRIEF DESCRIPTION OF THE DRAWINGS

This disclosure may best be understood by reference to the following description taken in conjunction with the accompanying drawings, in which like reference numerals identify like elements in the figures, and in which:

FIG. 2 is a diagram of a pumping system for two of the containers shown in FIG. 1 in accordance with the present disclosure;

FIG. 3A is a diagrammatic view of a user interface touch screen for controlling the pumping system shown in FIG. 2;

FIG. 3B is a diagrammatic view of a controller for the pumping system in FIG. 2.

DESCRIPTION OF THE PREFERRED EMBODIMENTS

It will be understood that the present methods and apparatus may be embodied in other specific forms without departing from the spirit of the disclosure. The present examples and embodiments, therefore, are to be considered in all respects as illustrative and not restrictive, and the scope of the disclosure is not to be limited to the details presented herein.

The apparatus of the present disclosure detects an empty fluid supply container by continuously analyzing its change in weight over short intervals. Thus, it can accurately detect an empty container regardless of the size, volume, or material (plastic or glass) of the container. This is especially important in therapeutic plasma exchange (TPE) procedures, since TPE operators may use many different replacement fluid supply container configurations and/or pump flow rates during a single blood collection procedure.

Figure 1:
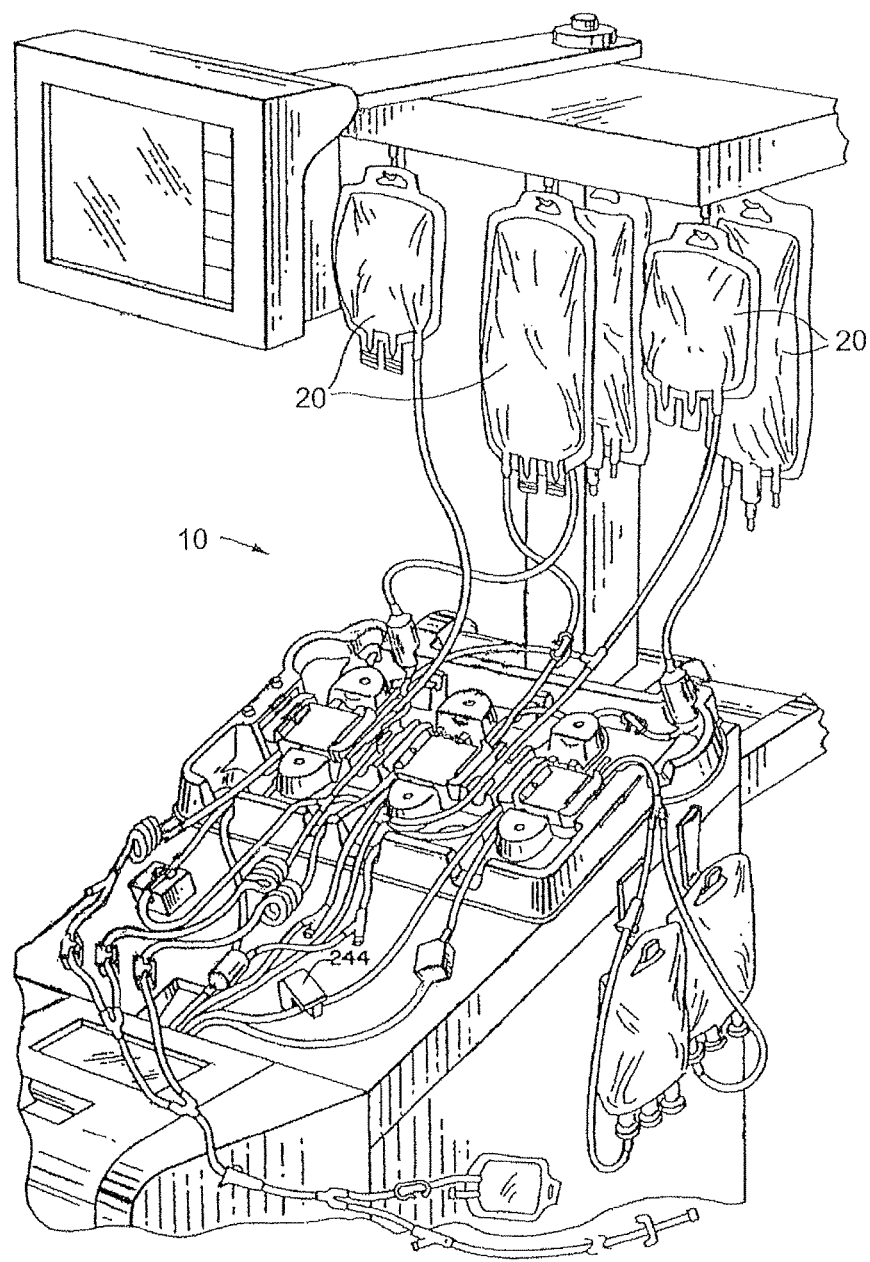
FIG. 1 is a perspective view of a blood processing system with a plurality of containers hanging therefrom.

FIG. 1 shows a blood processing system 10, which is particularly well-suited for processing whole blood. A number of containers 20 are suspended on hangers on the system 10. Some of the containers 20 may be fluid supply containers that dispense liquids to a blood donor during a blood collection procedure.

FIG. 2 illustrates a monitoring system, generally designated 200, in accordance with the present disclosure. In the example of FIG. 2, a pump 202 is turning in a counterclockwise direction and fluid is drawn from a first fluid supply container 204 which is suspended from a first scale 206 and through a first valve 210 that is in an open condition. If the operator uses a user interface touch screen 302 in FIG. 3A, such as by touching a "Switch Containers" button or field 304, a controller 310 in FIG. 3B receives a signal on controller input line 314 and sends a signal via an output line 312 to command the pump 202 to stop turning, i.e., to stop pumping. A second valve 211, which was initially in a closed condition, is then opened, and the first valve 210, which was initially open, is then closed. The controller 310 then commands the pump 202 to turn in a clockwise direction to draw fluid from the second fluid supply container 205 which is suspended from the second scale 207. In accordance with the present disclosure, if the operator does not touch the "Switch Containers" button or field 304 and the first fluid supply container 204 on the first scale 206 empties, the controller 310 will automatically detect the empty container and perform the operation to switch from which container the pump is drawing fluid.

Figure 4:
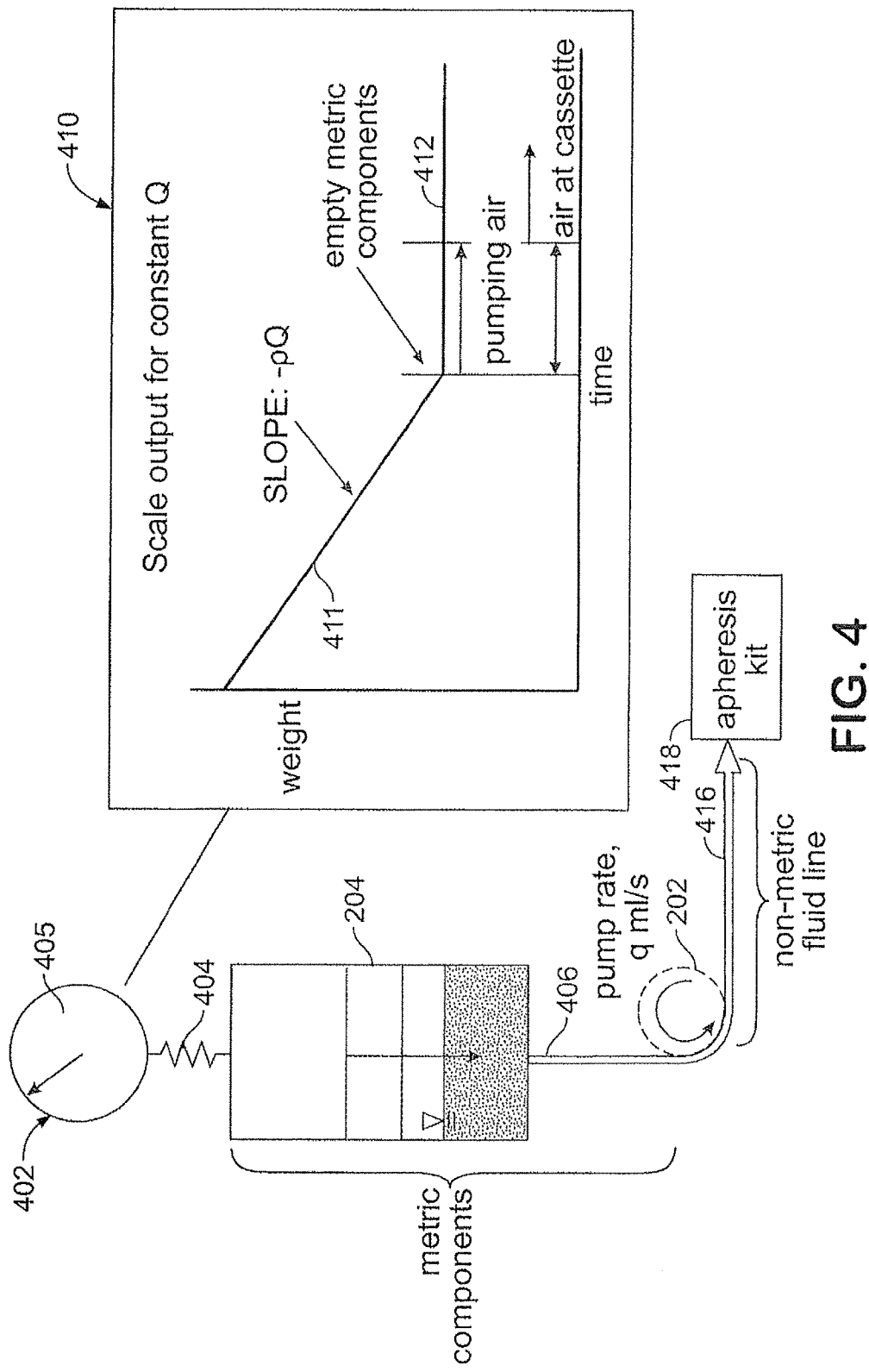
FIG. 4 is a diagrammatic view of the control of the pump in FIG. 2 by means of monitoring the rate of change of the weight of a container as it is being emptied by the pump.

FIG. 4 illustrates the control of the pump 202 in FIG. 2 by means of monitoring the rate of change of the weight of a container as it is being emptied by the pump. A scale 402, represented by a spring 404 and a dial 405, is used by the controller 310 to continuously monitor the weight of the metric components. The metric components include the fluid within the first fluid supply container 204, the first container 204 itself, the tubing 406, and possibly a drip chamber (not shown) that may be suspended from the scale 402. The system also includes non-metric components, such as the replacement fluid line 416, and perhaps a small reservoir (not shown), that do not hang from the scale, and which lead to the disposable kit 418.

When the pump 202 removes fluid from the first fluid supply container 204 at a rate of Q milliliters each second, the output weight indicated by the scale 402 continuously changes with time as shown by an angular line portion 411 of graph 410. When the metric components are empty, the weight determined by the scale 402 "flat lines," i.e. stops changing, as indicated by the horizontal line portion 412 of graph 410. When the procedure reaches the horizontal line portion 412 of graph 410, air will be drawn into the non-metric fluid line 416. Thus, it is important to recognize when the "flat line" 412 begins. Unfortunately, noise in the output signal of the scale 402 may make it impossible to determine from the scale data alone the exact time at which the rate of change in the weight becomes zero, especially at low flow rates.

Preferably, to overcome this noise issue, the controller 310 may monitor both the weight reading that is output from the scale 402, and the volume of fluid delivered by the pump 202 over a predefined, pump-volume dependent period, or pump-unit interval. During every pump-unit interval, the controller 310 compares the scale's weight change over the pre-defined period to the volume pumped during that period. If the ratio of the two values (weight change divided by pump volume) is less than about 0.5 for two consecutive intervals, the controller 310 indicates that the fluid supply container is empty and commands the pump 202 to stop pumping. It should be appreciated that the ratio of the two values when the fluid supply container is not empty should be one. When the fluid supply container is empty, the ratio should be zero. Thus, use of an intermediate value, such as 0.5, assists in minimizing any false determinations due to noise.

To avoid pumping air into the disposable kit 418, the scale flat line must be identified and the pump 202 stopped before the pump 202 can move fluid the full length of the non-metric portion of the replacement fluid line 416. Given a fluid line 416 length L (in inches) that is V milliliters/inch (ml/in) in volume, and a pump rate of q milliliters/second (ml/s), the maximum response time must be $tr=LV/q$ s. If the scale has a minimum resolution of w grams (g), then the weight monitoring of the scale output must allow for a weight change of at least w. Given the replacement fluid density $\rho$ grams/milliliter (g/ml) and a pump rate of q ml/s, the minimum detection period is $td=w/(\rho*q)$ s. Accordingly, to insure that air will not be pumped past the disposable kit 418, the ratio tr/td (response time available to response time required) must be greater than 1, i.e., $LV/q \div w/(\rho*q)=LV\rho/w>1$. Thus, where ID is an internal diameter for a tubing or replacement fluid line 416, then if ID=0.126", and V=0.2045 ml/in, for a high capacity scale having w=5 g, assuming $\rho$=1 g/ml, then for L(0.2045)(1)/5>1 it must be that L>25". That is, the non-metric portion of tubing L, which is the replacement fluid line 416, must be >25" in length to respond in time to stop the pump 202 so as to prevent the air from reaching the disposable kit 418.

Looking at two different examples of pump flow rates for a procedure, relatively low and relatively high, one could also determine the response time required, if given the other variables. Thus, if for example, the pump flow rate is 25 ml/min (0.417 ml/s) and the length L of the non-metric line 416 is 22", the response time, or time permitted between when a container would be empty and when air would begin to be pumped into the disposable kit 418, would be represented by tr=LV/q=22*0.2045/0.417≈11 s. Similarly, if for example, the pump flow rate is 80 ml/min (1.333 ml/s) and the other variables remain the same, the response time would be represented by tr=LV/q=22*0.2045/1.333≈4 s.

Further, to try to capture the moment at which the first fluid supply container 204 empties it is desired to identify the point in time at which the slope of the scale time trace changes to 0, or surpasses a defined threshold. Calculating the scale slope must rely on a discrete backward difference formula. Given that the minimum resolution of the scale 402 is w g, the minimum time over which the discrete difference stencil must be applied is ts>w/ρq. Thus, for the lower example flow rate of 25 ml/min (0.417 ml/s) and assuming ρ 1 g/ml, and a scale resolution of w=5 g, the difference stencil must cover at least 5/(1*0.417)≈11 s. For the higher example flow rate of 80 ml/min (1.333 ml/s) and assuming ρ 1 g/ml, and a scale resolution of w=5 g, the difference stencil must cover at least 5/(1*0.417)≈4 s. Thus, the sampling rates for the scale must be suitable to avoid air ingestion, as an alternative, a longer time interval would be available for a non-metric replacement fluid line 416 having a longer length L.

While particular embodiments have been shown and described, it will be obvious to those skilled in the art that changes and modifications may be made therein without departing from the disclosure in its broader aspects.

What is claimed is:

1. A method of determining when a fluid supply container of a blood processing system becomes empty by operation of a pump, the method comprising:
    providing a first fluid supply container adapted to be in communication with a patient when a first valve is in an open condition;
    monitoring a rate of change of weight of the first fluid supply container over a pump-unit interval;
    monitoring the volume of fluid delivered by the pump over the pump-unit interval;
    obtaining a ratio of the rate of change of weight of the first fluid supply container over the pump-unit interval to the volume of fluid delivered over the pump-unit interval; and
    stopping the operation of the pump when the ratio is less than a predetermined value.

2. The method of claim 1 wherein when upon determining that the ratio is less than the predetermined value further moving the first valve to a closed condition.

3. The method of claim 2 further comprising:
    providing a second fluid supply container adapted to be in communication with a patient when a second valve is in an open condition; and
    moving the second valve to an open condition upon determining that the ratio is less than the predetermined value.

4. The method of claim 3 further comprising:
    measuring the weight of the second fluid supply container while it is being emptied by a pump that is pumping fluid from the second fluid supply container into the patient;
    monitoring a rate of change of weight of the second fluid supply container over a second pump-unit interval;
    monitoring the volume of fluid delivered by the pump over the second pump-unit interval;
    obtaining a ratio of the rate of change of weight of the second fluid supply container over the second pump-unit interval to the volume of fluid delivered over the secondpump-unit interval; and
    stopping the operation of the pump when the ratio for the second fluid supply container is less than the predetermined value.

5. The method of claim 4 wherein when upon determining that the ratio for the second container is less than the predetermined value further moving the second valve to a closed condition.

6. A method of determining when a fluid supply container of a blood processing system becomes empty, the method comprising:
    providing a first fluid supply container adapted to be in communication with a patient when a first valve is in an open condition;
    monitoring a rate of change of weight of the first fluid supply container over two or more pump-unit intervals while it is being emptied by a pump that is pumping fluid from the first fluid supply container into the patient;
    obtaining a ratio of the rate of change of the weight of the first fluid supply container over two or more pump-unit intervals to a volume of fluid delivered by the pump during the two or more pump-unit intervals; and
    stopping the operation of the pump when the ratio is determined to be less than a predetermined value.

7. The method of claim 6 wherein the operation of the pump is stopped if the ratio is less than about 0.5 for two consecutive pump-unit intervals.

8. The method of claim 7 wherein when upon determining that the ratio is less than about 0.5 for two consecutive pump-unit intervals further moving the first valve to a closed condition.

9. The method of claim 8 further comprising:
    providing a second fluid supply container adapted to be in communication with a patient when a second valve is in an open condition; and
    moving the second valve to an open condition upon determining that the ratio is less than about 0.5 for two consecutive pump-unit intervals.

10. The method of claim 9 further comprising:
    monitoring a rate of change of the weight of the second fluid supply container over a second two or more pump-unit intervals while it is being emptied by a pump that is pumping fluid from the second fluid supply container into the patient;
    obtaining a ratio of the rate of change of the weight of the second fluid supply container over the second two or more pump-unit intervals to a volume of fluid delivered by the pump during the second two or more pump-unit intervals; and
    stopping the operation of the pump when the ratio for the second fluid supply container is less than the predetermined value.

11. The method of claim 10 wherein the ratio is determined to be less than the predetermined value if the ratio is less than about 0.5 for two consecutive pump-unit intervals.

12. The method of claim 9 wherein when upon determining that the ratio is less than the predetermined value further moving the second valve to a closed condition.

\* \* \* \* \*